United States Patent
Katsuhara et al.

(10) Patent No.: US 12,422,799 B2
(45) Date of Patent: Sep. 23, 2025

(54) STATE PREDICTION SYSTEM, MEMBER DETERMINATION SYSTEM, AND STATE PREDICTION METHOD

(71) Applicant: TOYOTA JIDOSHA KABUSHIKI KAISHA, Toyota (JP)

(72) Inventors: Yasuo Katsuhara, Susono (JP); Tomoya Takatani, Nisshin (JP); Hayato Yamaguchi, Susono (JP)

(73) Assignee: TOYOTA JIDOSHA KABUSHIKI KAISHA, Toyota (JP)

(*) Notice: Subject to any disclaimer, the term of this patent is extended or adjusted under 35 U.S.C. 154(b) by 549 days.

(21) Appl. No.: 17/948,590

(22) Filed: Sep. 20, 2022

(65) Prior Publication Data
US 2023/0107401 A1    Apr. 6, 2023

(30) Foreign Application Priority Data
Oct. 1, 2021    (JP) .................... 2021-163089

(51) Int. Cl.
G05B 13/04    (2006.01)
G05B 15/02    (2006.01)

(52) U.S. Cl.
CPC ........... *G05B 13/048* (2013.01); *G05B 15/02* (2013.01)

(58) Field of Classification Search
CPC ........................... G05B 15/02; G05B 13/048
USPC ........................................................ 700/44
See application file for complete search history.

(56) References Cited

U.S. PATENT DOCUMENTS

| | | | |
|---|---|---|---|
| 10,187,388 B2* | 1/2019 | Higgins | H04W 12/08 |
| 2009/0136909 A1* | 5/2009 | Asukai | A61B 5/7246 434/236 |
| 2013/0053086 A1* | 2/2013 | Akitomi | G06Q 10/0639 455/517 |
| 2015/0220613 A1* | 8/2015 | Tsubouchi | G06Q 10/10 707/746 |
| 2016/0128617 A1* | 5/2016 | Morris | G06Q 10/103 434/236 |
| 2019/0139438 A1 | 5/2019 | Tu et al. | |

FOREIGN PATENT DOCUMENTS

| | | | | |
|---|---|---|---|---|
| CN | 106295702 A | * | 1/2017 | ......... G06K 9/6277 |
| CN | 108650614 A | * | 10/2018 | ......... G06Q 10/04 |
| CN | 108650614 B | * | 7/2020 | ......... G06Q 10/04 |
| EP | 3992877 A1 | * | 5/2022 | ......... G06Q 10/10 |
| JP | 2011-186521 A | | 9/2011 | |
| JP | 2018-139087 A | | 9/2018 | |
| JP | 2019-087257 A | | 6/2019 | |
| JP | 7068215 B2 | * | 5/2022 | |
| TR | 201614979 A1 | * | 5/2018 | |
| WO | WO-2019000073 A1 | * | 1/2019 | ......... A61B 5/02055 |

* cited by examiner

*Primary Examiner* — Ronald D Hartman, Jr.
(74) *Attorney, Agent, or Firm* — Dinsmore & Shohl LLP

(57) ABSTRACT

A state prediction system includes a controller. The controller is configured to acquire a current state value indicating a current state of a targeted individual in a group. The controller is configured to acquire a state propagation amount indicating a state amount propagated from another person in the group to the targeted individual by communication between the targeted individual and the other person. The controller is configured to predict a future state value indicating a future state of the targeted individual from the acquired current state value of the targeted individual and the acquired state propagation amount.

8 Claims, 8 Drawing Sheets

PRESENT (TIME t) → PREDICTION → FUTURE (TIME t + 1)

Sm > Th

PRESENT (TIME t)
AFTER PROPOSAL

FUTURE (TIME t + 1)

Sm ≤ Th

PRESENT (TIME t)

FUTURE (TIME t + 1)

| | CONVERSATION AMOUNT $W_{ij}(t)$ | | | | FUTURE STRESS STATE VALUE OF INDIVIDUAL $S_1(t+1)$ TO $S_k(t+1)$ | | | | FUTURE STRESS STATE VALUE OF GROUP |
|---|---|---|---|---|---|---|---|---|---|
| | $W_{12}(t)$ | $W_{13}(t)$ | $W_{14}(t)$ | ... | $S_1(t+1)$ | $S_2(t+1)$ | ... | $S_k(t+1)$ | $S_m$ |
| PATTERN 1 | 0.1 | 0.1 | 0.1 | ... | 0.5 | 0.3 | ... | 0.2 | 0.1 |
| PATTERN 2 | 0.1 | 0.1 | 0.2 | ... | 0.6 | 0.2 | ... | 0.5 | 0.9 |
| PATTERN 3 | 0.1 | 0.1 | 0.3 | ... | 0.1 | 0.4 | ... | 0.5 | 0.4 |
| ⋮ | ⋮ | ⋮ | ⋮ | | ⋮ | ⋮ | ⋮ | | ⋮ |

STATE PREDICTION SYSTEM, MEMBER DETERMINATION SYSTEM, AND STATE PREDICTION METHOD

CROSS-REFERENCE TO RELATED APPLICATION

This application claims priority to Japanese Patent Application No. 2021-163089 filed on Oct. 1, 2021, incorporated herein by reference in its entirety.

BACKGROUND

1. Technical Field

The present disclosure relates to a state prediction system, a member determination system and a state prediction method.

2. Description of Related Art

Japanese Unexamined Patent Application Publication No. 2011-186521 (JP 2011-186521 A) discloses an emotion estimation device that estimates a group emotion, which is an emotion in a human communication place. In the technique, the group emotion is estimated from information on current emotions of individuals and state transition models.

SUMMARY

In the technique of JP 2011-186521 A, it can be estimated that the current group emotion deteriorates due to the deterioration of the current emotions of individuals, but it is not possible to take any measures before the group emotion deteriorates. It may be difficult to restore the atmosphere of the place even if measures are taken from a state where the group emotion deteriorates. Accordingly, it is desirable to predict a future state of an individual in order to smoothly promote communication in a group.

The present disclosure provides a technique capable of predicting a future state of an individual in a group.

A first aspect of the present disclosure relates to a state prediction system including a controller. The controller is configured to acquire a current state value indicating a current state of a targeted individual in a group, acquire a state propagation amount indicating a state amount propagated from another person in the group to the targeted individual by communication between the targeted individual and the other person, and predict a future state value indicating a future state of the targeted individual from the acquired current state value of the targeted individual and the acquired state propagation amount.

In the aspect, the controller may be configured to acquire, as information, a current state value indicating a current state of the other person, a current communication amount between the targeted individual and the other person, and a degree of influence of the other person on a state of the targeted individual, and derive the state propagation amount from the other person to the targeted individual based on the acquired information.

In the aspect, the controller may be configured to derive, as the state propagation amount from the other person to the targeted individual, a product of the current state value of the other person, the current communication amount between the targeted individual and the other person, and the degree of the influence of the other person on the state of the targeted individual, and derive, as the future state value of the targeted individual, a sum of the current state value of the targeted individual and the state propagation amount from the other person to the targeted individual.

In the aspect, the controller may be configured to, for each of a plurality of other persons in the group, derive, as the state propagation amount from the other person to the targeted individual, a product of the current state value of the other person, the current communication amount between the targeted individual and the other person, and the degree of the influence of the other person on the state of the targeted individual, and derive, as the future state value of the targeted individual, a total sum of the current state value of the targeted individual and state propagation amounts from the other persons to the targeted individual.

In the aspect, the controller may be configured to, for each of a plurality of other persons in the group, acquire the state propagation amount from the other person to the targeted individual, and compare the acquired state propagation amounts from the other persons to the targeted individual and, based on a comparison result, propose a change in a communication amount between the targeted individual and the other person such that the future state value of the targeted individual is improved.

In the aspect, the controller may be configured to predict a future state value of each of a plurality of persons in the group, and predict a future group state value indicating a future state of the group based on the predicted future state value of each of the persons.

In the aspect, the controller may be configured to derive a target communication amount between the persons such that the predicted future group state value is improved, and compare a current communication amount between two targeted persons in the group with the target communication amount and propose a change in a communication amount based on a comparison result.

A second aspect of the present disclosure relates to a member determination system including a controller. The controller is configured to temporarily set a plurality of persons who are candidates that constitute a group, for each of the temporarily set persons, acquire a current state value indicating a current state of the person, for each of the temporarily set persons, acquire a state propagation amount indicating a state amount propagated from another person in the group to the person, the state amount being predicted based on a past communication amount between the person and the other person, for each of the temporarily set persons, predict a future state value indicating a future state of the person from the acquired current state value of the person and the acquired state propagation amount to the person, predict a future group state value indicating a future state of the group based on the predicted future state value of each of the persons, and when the predicted future group state value satisfies a predetermined condition for a good state, determine the temporarily set persons as members of the group.

A third aspect of the present disclosure relates to a state prediction method that is executed by a computer. The state prediction method includes acquiring a current state value indicating a current state of a targeted individual in a group, acquiring a state propagation amount indicating a state amount propagated from another person in the group to the targeted individual by communication between the targeted individual and the other person, and predicting a future state value indicating a future state of the targeted individual from the acquired current state value of the targeted individual and the acquired state propagation amount.

According to the aspects of the present disclosure, it is possible to provide a technique capable of predicting a future state of an individual in a group.

BRIEF DESCRIPTION OF THE DRAWINGS

Features, advantages, and technical and industrial significance of exemplary embodiments of the present disclosure will be described below with reference to the accompanying drawings, in which like signs denote like elements, and wherein.

DETAILED DESCRIPTION OF EMBODIMENTS

First Embodiment

Figure 1:
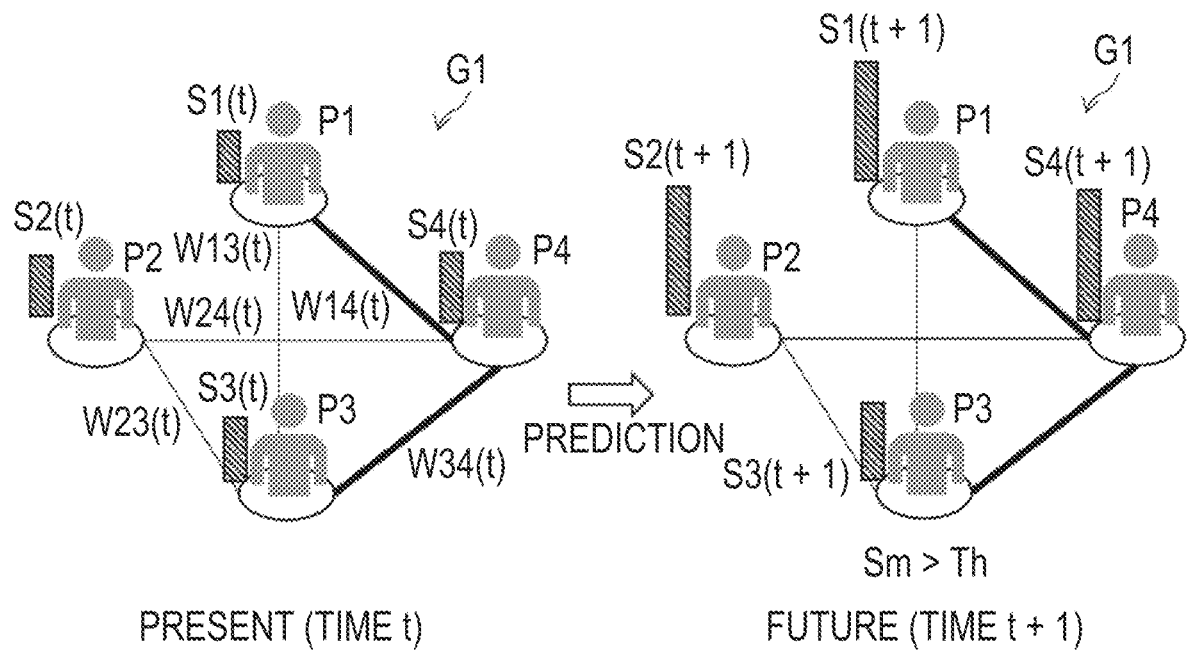
FIG. 1 is a diagram for describing a function of a communication support system according to a first embodiment.

FIG. 1 is a diagram for describing a function of a communication support system according to a first embodiment. The communication support system supports smooth communication in a group G1 of FIG. 1. The smooth communication means that each of members P1 to P4 (hereinafter, also referred to as "individual" or "person") that constitute the group G1 communicates while the member maintains a good state. The number of members may be plural. Hereinafter, an example in which the group G1 has a meeting will be schematically described. The detailed processing of the system will be described later.

The communication support system periodically acquires current state values $S1(t)$ to $S4(t)$ indicating current states of respective members P1 to P4 of the group G1, and current communication amounts between two members $W12(t)$, $W13(t)$, $W14(t)$, $W23(t)$, $W24(t)$, $W34(t)$ in each of a plurality of combinations for any two members drawn from the group G1. Let the present be time t. For example, the current state value $S1(t)$ is a numerical value representing a current state of the member P1, and the communication amount $W13(t)$ is a numerical value representing a current communication amount between the members P1 and P3. There is no communication between the members P1, P2, and the communication amount $W12(t)$ therebetween is zero. In the example of FIG. 1, the sizes of the current state values $S1(t)$ to $S4(t)$ are represented by lengths of bar graphs, and the sizes of the communication amount $W13(t)$ and the like are represented by the thickness of a solid line between members.

The current state value is, for example, a stress state value, an emotional value, a performance value, a value representing the degree of fatigue, a value representing the degree of happiness, and the like. The current state value may be a value obtained by substituting at least two of the values into a predetermined calculation formula. The predetermined calculation formula may be, for example, a formula for calculating the total sum by weighting each value. The current state value can be detected by a known technique using a sensor or the like. For example, the emotional value may be acquired by analyzing an image of a member captured by a camera, executing facial expression analysis of the member, and estimating the emotions of the member. The current state value does not have to be a detected value, and may be a numerical value reported by each member.

The current state value is, for example, a value in the range from negative to positive, where a larger positive value represents a worse state and a smaller negative value represents a better state. For example, when the current state value represents a stress state value, a larger positive value represents a worse state and a smaller negative value represents a better state. It may be also possible that a larger positive value represents a better state and a smaller negative value represents a worse state. For example, when the current state value represents happiness, a larger positive value represents a better state and a smaller negative value represents a worse state.

The communication amount is a numerical value of the degree of communication between two members per unit time, such as the conversation amount between two members per unit time, the amount derived based on the time when one of two members smiles at the other per unit time, the amount derived based on the time when one of the two members sees the other per unit time, or the amount derived based on the amount of time gestures are made between two members per unit time. The communication amount may be a value obtained by substituting at least two of the amounts into a predetermined calculation formula. The communication amount is a value of zero or more. The communication amount can be detected by a known technique by using a microphone, a camera, a sensor, or the like.

The communication support system acquires the state propagation amount between two members in each of combinations for any two members drawn from the group G1 based on the current state values $S1(t)$ to $S4(t)$ and the current communication amounts $W12(t)$ to $W34(t)$. The state propagation amount indicates the state amount propagated from one member to the other member by communication of two members, and is a value in the range of negative to positive. The state propagation amount from a first member to a second member may be proportional to, for example, the current state value of the first member and the current communication amount between the members. The state propagation amount from the first member to the second member may be further proportional to a coefficient representing susceptibility of the second member to the state of a partner. Therefore, for example, the state propagation amount from the member P1 to the member P3 has a high probability of being different from the state propagation amount from the member P3 to the member P1. Since the communication amount W12($t$) between the member P1 and the member P2 is zero, it is assumed that the state propagation amount from the member P1 to the member P2 and the state propagation amount from the member P2 to the member P1 are zero.

For each of the members P1 to P4, the communication support system predicts a future state value indicating the future state of the member from the current state values S1($t$) to S4($t$) of the member and the state propagation amounts from a plurality of other members to the member. Let the future be time t+1. For example, a future state value S1($t$+1) is a numerical value representing the future state of the member P1, and may be obtained by adding the state propagation amount from the member P2 to P1, the state propagation amount from the member P3 to P1, and the state propagation amount from the member P4 to P1 to the current state value S1($t$) of the member P1. Future state values S2($t$+1) to S4($t$+1) can also be acquired in the same manner.

The communication support system predicts a group state value Sm indicating the future state of the group G1 based on the future state values S1($t$+1) to S4($t$+1). In the example of FIG. 1, it is assumed that the future group state value Sm is larger than a threshold value Th. When the group state value Sm is larger than the threshold value Th, the communication support system proposes to the members P1 to P4 to change the communication amount such that the future group state value Sm is smaller than the threshold value Th.

For example, the communication support system proposes increase in the communication amounts between the member P1 and the member P2, between the member P1 and the member P3, between the member P2 and the member P3, and between the member P3 and the member P4, and proposes decrease in the communication amounts between member the P1 and the member P4, and between the member P2 and the member P4.

Figure 2:
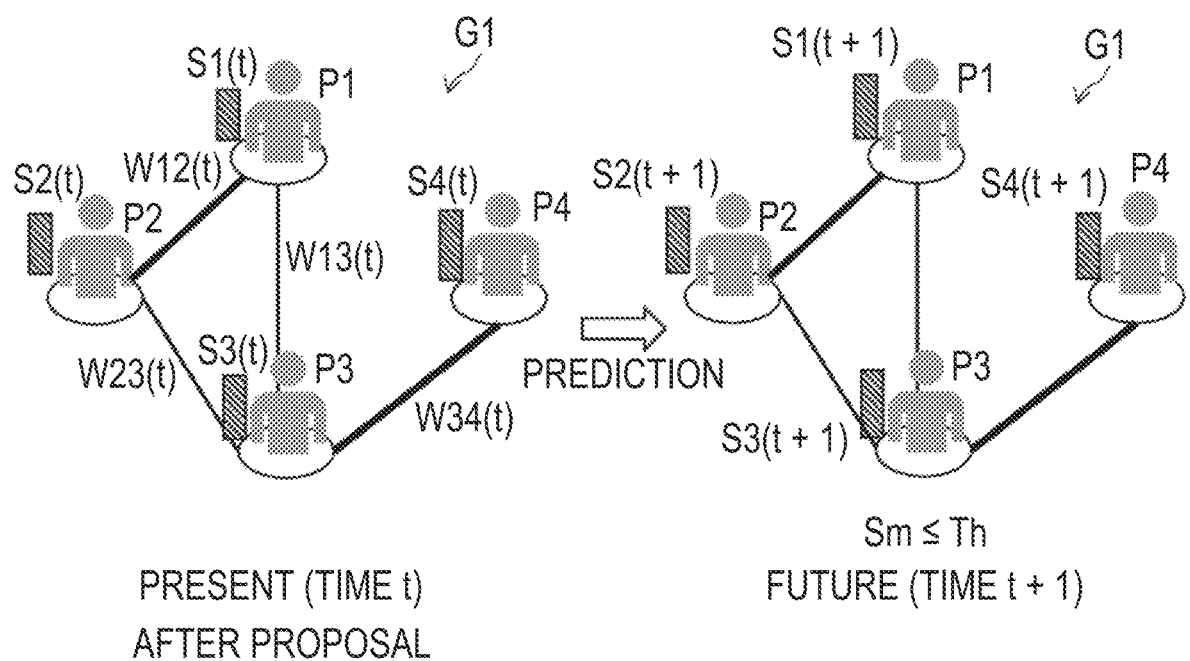
FIG. 2 is a diagram for describing the function of the communication support system following FIG. 1.

FIG. 2 is a diagram for describing the function of the communication support system following FIG. 1. It is assumed that each of the members P1 to P4 changes the communication amounts according to the proposal from the communication support system. As a result, the future state values S1($t$+1) to S4($t$+1) of the members newly predicted by the communication support system are different from the values in FIG. 1. The future group state value Sm is also smaller than the threshold value Th, unlike the value in FIG. 1. Therefore, as compared with the state of FIG. 1, it is easy for each member to maintain a good state during the meeting, and thus communication in the group G1 can be promoted more smoothly.

Hereinafter, an example in which the current state value and the future state value are stress state values and the communication amount is the conversation amount will be described in detail. The stress state value is, for example, a value in the range of negative to positive, where a larger positive value represents a stronger stress and a smaller negative value represents a greater degree of relaxation. The stress state represented by positive and negative may be reversed. The conversation amount is a value of zero or more.

Figure 3:
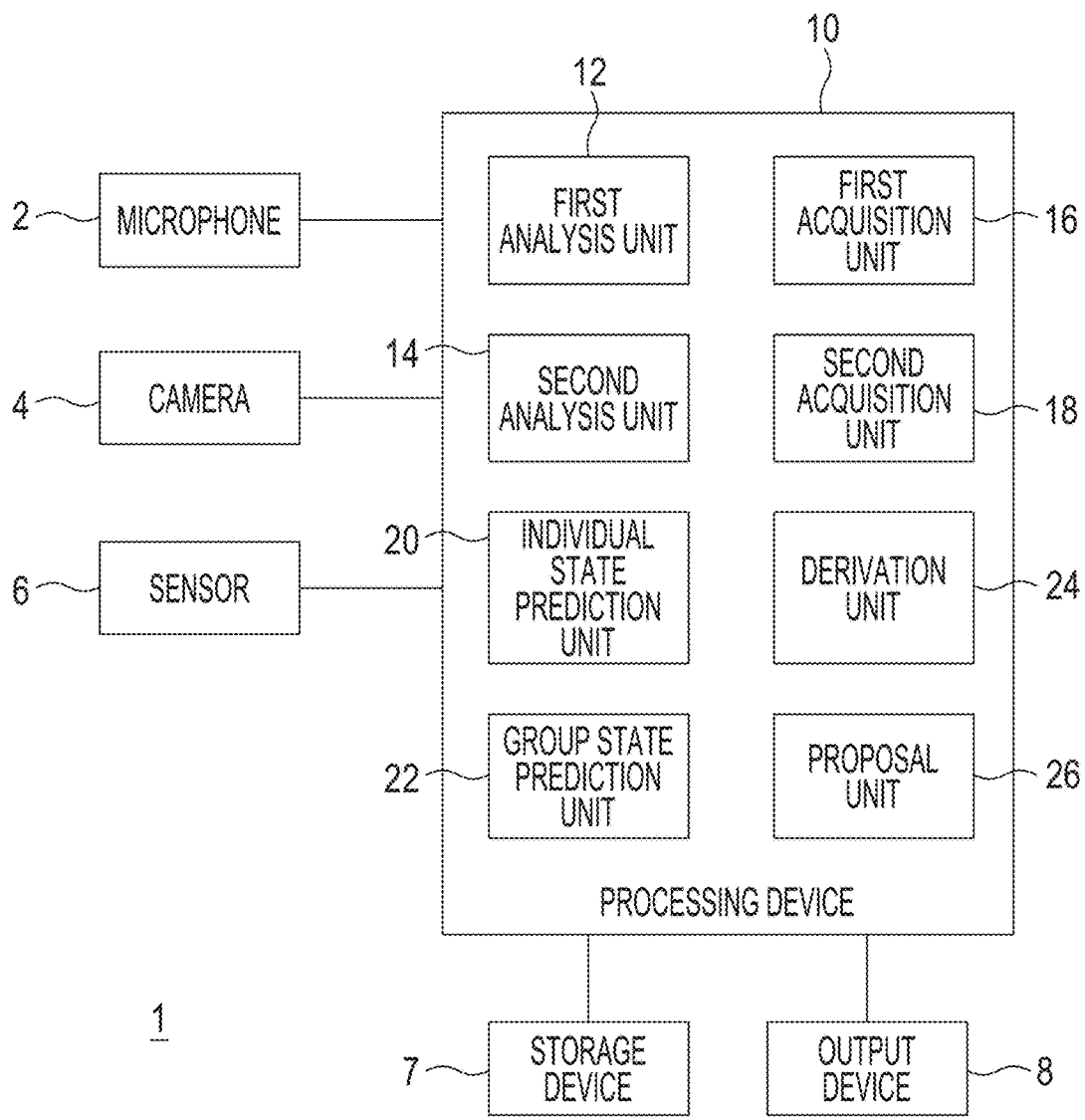
FIG. 3 is a diagram showing a configuration of the communication support system according to the first embodiment.

FIG. 3 is a diagram showing a configuration of the communication support system 1 according to the first embodiment. The communication support system 1 includes a microphone 2, a camera 4, a sensor 6, a storage device 7, an output device 8, and a processing device 10. Although not shown, the communication support system 1 has a plurality of the microphones 2, a plurality of the cameras 4, and a plurality of the sensors 6. The communication support system 1 can also be called a "state prediction system". The processing device 10 is an example of the controller in the present disclosure.

The microphone 2 acquires conversations of a plurality of members P1 to Pk (k is an integer of two or more) that constitute the group G1 and supplies the acquired voice data to the processing device 10. The camera 4 captures the members P1 to Pk, and supplies the captured image data to the processing device 10. The sensor 6 is attached to the body of each of the members P1 to Pk, detects the heart rate of each of the members P1 to Pk, and supplies the detected heart rate data to the processing device 10. The output device 8 includes, for example, at least one of a display capable of outputting images and a voice output device capable of outputting voices to output various information. The output device 8 may be included in a mobile terminal, such as a smartphone possessed by each of the members P1 to Pk.

The processing device 10 includes a first analysis unit 12, a second analysis unit 14, a first acquisition unit 16, a second acquisition unit 18, an individual state prediction unit 20, a group state prediction unit 22, a derivation unit 24, and a proposal unit 26. The processing device 10 may be, for example, a personal computer, a smartphone, a server device, or the like.

The configuration of the processing device 10 can be implemented by the CPU, memory, or other LSI of a computer in terms of hardware, and can be implemented by a program loaded in memory in terms of software, but here, functional blocks implemented by cooperation of hardware and software are drawn. Therefore, it is understood by those skilled in the art that the functional blocks can be implemented in various forms by one of a hardware, a software, or a combination thereof.

The second analysis unit 14 has a face image recognition function and identifies which registered user's face image a plurality of face images captured by the camera 4 represents. The storage device 7 stores the feature amount of the face image of the registered user. The second analysis unit 14 compares the feature amount of the face image of the registered user stored in the storage device 7 with the feature amount of the face image of the image data, executes an authentication process of the face image of each of the members P1 to Pk, and decides whether or not each of the members P1 to Pk is the registered user. When the second analysis unit 14 decides that each of the members P1 to Pk is the registered user, the second analysis unit 14 supplies the identification information about the registered users, which is the identification information for each of the members P1 to Pk, to the first analysis unit 12 and the second acquisition unit 18. Information for an administrator or the like to specify a plurality of members may be input to an input unit (not shown) of the processing device 10.

The second analysis unit 14 periodically detects the conversation amount Wij(t) (i, j≤k) between members Pi, Pj per unit time up to the present by performing voice analysis on voice data supplied from the microphone 2 and performing image analysis on image data supplied from the camera 4. For example, the second analysis unit 14 derives a larger conversation amount Wij(t) as the conversation time between the members Pi, Pj per unit time is longer. The second analysis unit 14 supplies the detected conversation amount Wij(t) to the second acquisition unit 18.

The second analysis unit 14 has a speaker recognition function and identifies which registered user's voice data the voice data supplied from the microphone 2 represents. A voice template of registered users is registered in the storage device 7, and the second analysis unit 14 compares the supplied voice data with the voice template stored in the storage device 7 to specify who the speaker is. The second analysis unit 14 specifies the position of each of the members P1 to Pk from the image data, and estimates, from the direction in which the face image of an uttering member is facing, to which member the utterance is addressed. The second analysis unit 14 may have a natural language processing function, and may analyze a conversation situation between members and estimate which members are talking with each other from the analysis result. A known technique can be used to detect the conversation amount Wij(t).

The first analysis unit 12 periodically detects the stress state values $S1(t)$ to $Sk(t)$ of each of the members P1 to Pk by analyzing heart rate data of each of the members P1 to Pk supplied from the sensor 6, and supplies the detected stress state values $S1(t)$ to $Sk(t)$ to the first acquisition unit 16 and the second acquisition unit 18. Known techniques can be used to detect the stress state values. It should be noted that the sensor 6 may not be provided and the degree of stress reported by each of the members P1 to Pk may be periodically input by an administrator or the like to an input unit (not shown) of the processing device 10 by numerical input or voice input. In this case, the first analysis unit 12 detects the stress state values $S1(t)$ to $Sk(t)$ by analyzing the input information.

The first acquisition unit 16 and the second acquisition unit 18 perform the following process for each of the members P1 to Pk of the group G1.

The first acquisition unit 16 acquires a current stress state value $Si(t)$ of a targeted member Pi detected by the first analysis unit 12. The operation is an example of the first acquisition unit 16 acquiring the current state value $Si(t)$ indicating the current state of the targeted individual Pi in the group G1.

The second acquisition unit 18 acquires, for each of the others in the group G1, a state propagation amount indicating a state amount propagated from the other person Pj to the targeted member Pi by communication between the targeted member Pi and the other person Pj in the group G1. Specifically, for each of a plurality of other persons in the group G1, the second acquisition unit 18 acquires the current stress state value $Sj(t)$ of the other person Pj detected by the first analysis unit 12, the current conversation amount $Wij(t)$ between the targeted member Pi and the other person Pj detected by the second analysis unit 14, and a degree of influence $\lambda$ of the other person Pj on the state of the targeted member Pi. The degree of influence $\lambda$ is a value assigned to the targeted member Pi. For each of the others in the group G1, the second acquisition unit 18 derives, as the state propagation amount from the other person Pj to the targeted member Pi, a product of the acquired current stress state value $Sj(t)$ of the other person Pj, the current conversation amount $Wij(t)$ between the targeted member Pi and the other person Pj, and the degree of influence $\lambda$ of the other person Pj on the state of the targeted member Pi.

The operation is an example of, for each of the other persons in the group G1, the second acquisition unit 18 acquiring the current state value $Sj(t)$ indicating the current state of the other person Pj, the current communication amount $Wij(t)$ between the targeted individual Pi and the other person Pj, and the degree of influence $\lambda$ of the other person Pj on the state of the individual Pi, and deriving, as the state propagation amount from the other person Pj to the individual Pi, the product of the acquired current state value $Sj(t)$ of the other person Pj, the current communication amount $Wij(t)$ between the individual Pi and the other person Pj, and the degree of influence $\lambda$ of the other person Pj on the state of the individual Pi.

The storage device 7 stores in advance the degree of influence $\lambda$ assigned to a registered user in association with identification information for the registered user. The degree of influence $\lambda$ is a value of zero or more. Since the degree of influence $\lambda$ differs depending on the individuality of the registered user, the degree of influence is set for each registered user. The second acquisition unit 18 acquires identification information for the targeted member, and acquires the degree of influence $\lambda$ associated with the acquired identification information from the storage device 7.

The degree of influence $\lambda$ may be set for each combination of an individual and another person. In this way, it is also possible to reflect, in the state propagation amount, a different degree of influence of the state of a partner to the individual depending on whether the partner is skillful or clumsy, thereby making it possible to acquire a more accurate state propagation amount.

The degree of influence $\lambda$ can change depending on the physical condition of the member and the like. As for the degree of influence $\lambda$, the numerical value reported by each of the members P1 to Pk before the meeting may be stored in the storage device 7 through input of administrator or the like into the processing device 10, or a value derived based on a detected value of a sensor (not shown) may be stored in the storage device 7. For example, the degree of fatigue or concentration of the members may be periodically detected by a sensor, and the degree of influence may be periodically derived according to the detection result by the processing device 10. Alternatively, a sleep time of the previous day and an average sleep time reported by the member may be input to the processing device 10, and the degree of influence may be derived based on the ratio of the sleep time of the previous day to the average sleep time by the processing device 10.

For each of the members P1 to Pk, the individual state prediction unit 20 predicts a future stress state value $Si(t+1)$ of the targeted member Pi, from the current stress state value $Si(t)$ of the targeted member Pi, which is acquired by the first acquisition unit 16, and state propagation amounts from the other persons to the targeted member Pi, which are acquired by the second acquisition unit 18. That is, the individual state prediction unit 20 predicts future state values $S1(t+1)$ to $Sk(t+1)$ of respective members P1 to Pk in the group G1. Specifically, for each of the members P1 to Pk, the individual state prediction unit 20 sets, as the future stress state value $Si(t+1)$ of the targeted member Pi, the total sum of the current stress state value $Si(t)$ of the targeted member Pi and the state propagation amounts from the other persons to the targeted member Pi.

The operation is an example of, for each of the persons P1 to Pk in the group G1, the individual state prediction unit 20 predicting the future state value $Si(t+1)$ indicating the future state of the individual Pi from the current state value $Si(t)$ of the individual Pi and the state propagation amounts from the other persons to the individual Pi.

Figure 4:
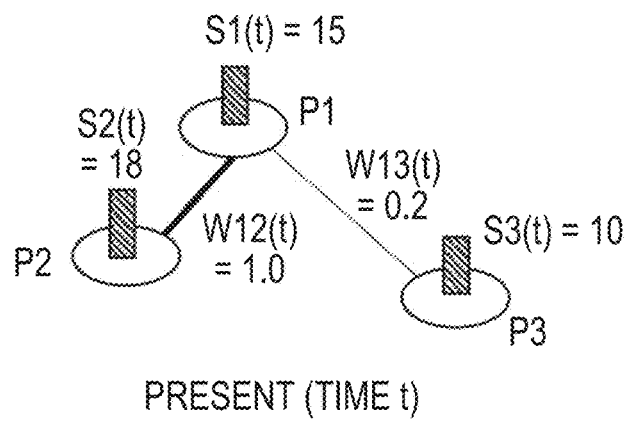
FIG. 4 is a diagram showing an example of current stress state values and conversation amounts of members.
Figures 5, 6:
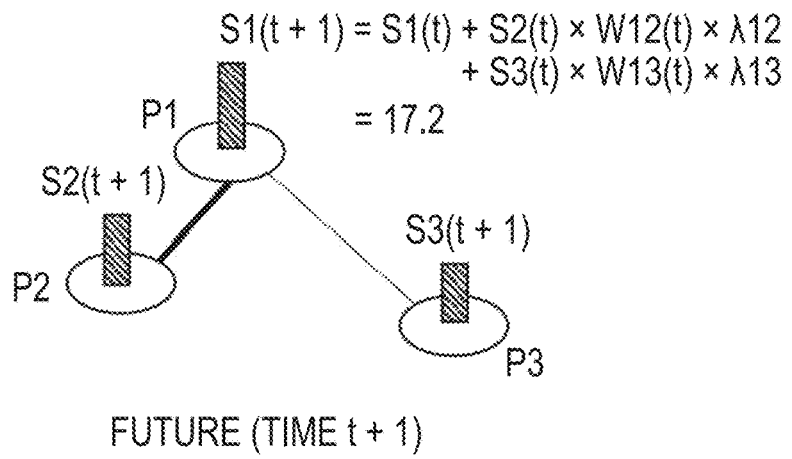
FIG. 5 is a diagram showing future stress state values predicted from the current stress state values and the conversation amounts of FIG. 4.
FIG. 6 is a diagram showing an example of a relationship between each of a plurality of conversation amount patterns, a future individual stress state value, and a future group stress state value.

FIG. 4 shows an example of the current stress state values and conversation amounts of the members P1 to P3. FIG. 5 shows future stress state values predicted from the current stress state values and the conversation amounts of FIG. 4.

In FIG. 4, it is assumed that the current stress state value $S1(t)$ of the member P1 is "15", the current stress state value $S2(t)$ of the member P2 is "18", and the current stress state value S3(t) of the member P3 is "10". It is assumed that the current conversation amount W12(t) between the member P1 and the member P2 is "1.0", and the current conversation amount W13(t) between the member P1 and the member P3 is "0.2", and the current conversation amount W23(t) between the member P2 and the member P3 is "0".

In the case of this example, the future stress state value S1(t+1) of the member P1 is expressed by the following equation (1) as described above.

$$S1(t+1)=S1(t)+S2(t)\times W12(t)\times \lambda 12+S3(t)\times W13(t)\times \lambda 13 \quad \text{Equation (1)}$$

Here, $\lambda 12$ is the degree of influence of the member P2 on the state of the member P1, and $\lambda 13$ is the degree of influence of the member P3 on the state of the member P1. As described above, $\lambda 12$ and $\lambda 13$ may be equal. $S2(t)\times W12(t)\times \lambda 12$ is the state propagation amount from the member P2 to the member P1. $S3(t)\times W13(t)\times \lambda 13$ is the state propagation amount from the member P3 to the member P1.

For example, assuming $\lambda 12=0.1$ and $\lambda 13=0.2$, S1(t+1) becomes "17.2". In this way, the future stress state value S1(t+1) of the member P1 can be predicted from the current stress state values S1(t) to S3(t) of the members P1 to P3 and the conversation amounts W12(t) and W13(t). Since the future state value of an individual is predicted based on the state propagation amounts, it is possible to predict the future state value of the individual in consideration of the influence of communication with other persons.

For example, when the stress state value Sj(t) of the communication partner Pj of a certain member Pi is negative, the state propagation amount from the partner Pj becomes a negative value, and thus, the future stress state value Si(t+1) of the member Pi becomes lower than the current stress state value Si(t). That is, when the partner is in a relaxed state, the stress state of the member is expected to be improved by the member being influenced by the state of the partner by communication with the partner.

For each of the members P1 to Pk, the individual state prediction unit 20 may predict the future state value Si(t+1) of the targeted member Pi based on the current state value of the targeted member Pi and the state propagation amount from one other person Pj to the targeted member Pi. That is, in a situation where the state propagation amounts from a plurality of other persons to the targeted member Pi is greater than 0, all the state propagation amounts do not have to be considered. In this case, the one other person Pj may be, for example, a member having the maximum absolute value of the state propagation amount to the targeted member Pi. There may be two or more others. Even if the state propagation amount having a relatively small absolute value is not used, by using the state propagation amount having the maximum absolute value, the deterioration of the prediction accuracy of the future state value can be suppressed. In addition, the processing load can be reduced.

The group state prediction unit 22 predicts the stress state value Sm of the group G1 indicating the future state of the group G1 based on the future stress state values S1(t+1) to Sk(t+1) of the respective members P1 to Pk predicted by the individual state prediction unit 20. The group state prediction unit 22 sets a statistical value of the respective future stress state values S1(t+1) to Sk(t+1) of the members P1 to Pk as the stress state value Sm of the group G1. The statistical value is, for example, an average value.

The operation is an example of the group state prediction unit 22 predicting the group state value Sm indicating the future state of the group G1 based on the future state values S1(t+1) to Sk(t+1) of the respective persons P1 to Pk predicted by the individual state prediction unit 20.

When the predicted future stress state value Sm of the group G1 is larger than a threshold Th, the derivation unit 24 derives a target conversation amount Wij_m(t) between the members P1 to Pk in the group G1 such that the predicted future stress state value Sm of the group G1 is improved. The threshold value Th can be appropriately set by an experiment or a simulation.

The operation is an example of the derivation unit 24 deriving the target communication amount between the persons P1 to Pk in the group G1 such that the predicted future group state value Sm is improved when the predicted future state value Sm of the group G1 satisfies a predetermined condition regarding a bad state.

The derivation unit 24 virtually sets patterns of a plurality of different conversation amounts, and for each of the patterns, derives the future stress state values S1(t+1) to Sk(t+1) of the respective members P1 to Pk based on the current stress state values S1(t) to Sk(t) of the respective members P1 to Pk, and derives the average value of the derived future stress state values S1(t+1) to Sk(t+1) as the stress state value Sm of the group G1. In this way, it is possible to estimate what kind of pattern of the conversation amounts makes the stress state value Sm of the group G1 smaller.

The derivation unit 24 sets the pattern of the conversation amount in which the stress state value Sm of the group G1 is minimized as the target conversation amount Wij_m(t) between the members P1 to Pk. The derivation unit 24 may set the pattern of the conversation amount in which the stress state value Sm of the group G1 is equal to or lower than a predetermined value as the target conversation amount Wij_m(t) between the members P1 to Pk.

FIG. 6 shows an example of a relationship between each of the conversation amount patterns, the future stress state values S1(t+1) to Sk(t+1) of the individual, and the future stress state value Sm of the group G1. In the example, the conversation amount patterns cover all combinations of numerical values such that the conversation amount Wij(t) differs by 0.1.

In the example of FIG. 6, it is assumed that the stress state value Sm of the group G1 is the minimum in a pattern 1 of the conversation amount. Therefore, the conversation amount Wij(t) of the pattern 1 is set as the target conversation amount Wij_m(t). Accordingly, for example, the target conversation amount W12_m(t) between the members P1, P2 is 0.1, the target conversation amount W13_m(t) between the members P1, P3 is 0.1, and the target conversation amount W14_m(t) between the members P1, P4 is 0.1.

When the stress state value Sm of the group G1 is larger than the threshold value Th, for each of combinations of two members Pi, Pj in the group G1, the proposal unit 26 compares the current conversation amount Wij(t) of two persons with the target conversation amount Wij_m(t), and proposes an increase in the conversation amount when the current conversation amount Wij(t) is smaller than the target conversation amount Wij_m(t) and proposes decrease in the conversation amount when the current conversation amount Wij(t) is larger than the target conversation amount Wij_m(t). The proposal unit 26 proposes a change in the conversation amount, for example, by causing the output device 8 to output an image or voice indicating the content of the proposal.

The operation is an example of the proposal unit 26, when the future group state value Sm is larger than the threshold value Th, comparing the current communication amount Wij(t) with the target communication amount Wij_m(t) with respect to the two targeted persons Pi, Pj in the group G1 and proposing the change in the communication amount based on the comparison result. In this way, it is possible to propose the change in the communication amount between two persons in the Group G1 such that the future state of the group G1 is less likely to deteriorate when the state is predicted to deteriorate. Therefore, it is possible to make the members find what measures should be taken to improve the future state of the group G1 more than predicted.

The proposal unit 26 does not propose the change in the conversation amount when the stress state value Sm of the group G1 is lower than the threshold value Th.

The processing device 10 periodically repeats the above process.

Figure 7:
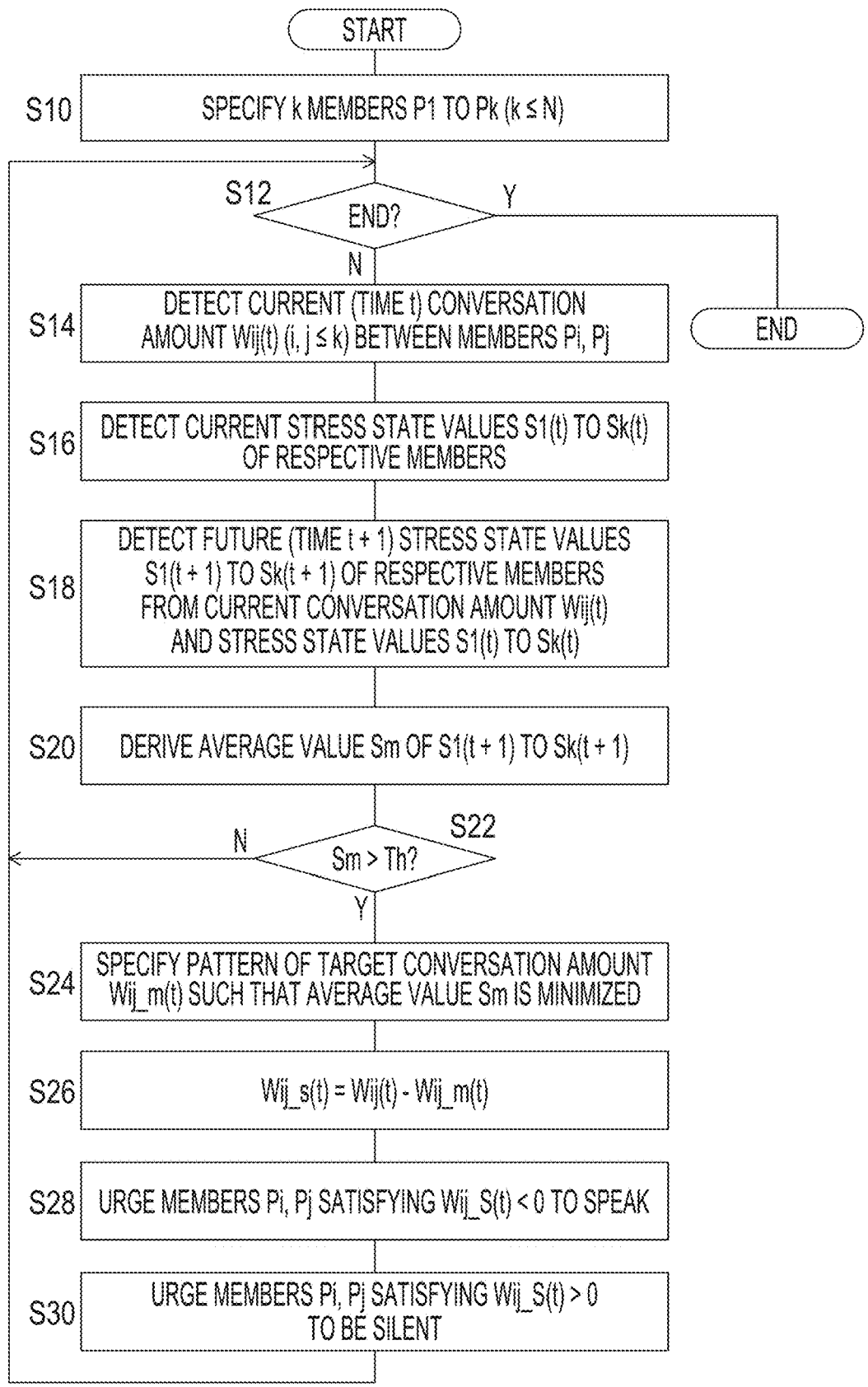
FIG. 7 is a flowchart showing a communication support process of the communication support system of FIG. 3.

FIG. 7 is a flowchart showing a communication support process of the communication support system 1 of FIG. 3. The process is started when a meeting is started.

The second analysis unit 14 specifies k members P1 to Pk (k≤N) (step S10), and when an instruction to end the process is not input (N in step S12), the second analysis unit 14 detects the current conversation amount Wij(t) (i, j≤k) between the members Pi, Pj (step S14). The first analysis unit 12 detects the current stress state values S1($t$) to Sk(t) of the respective members P1 to Pk (step S16), and the individual state prediction unit 20 derives the future stress state values S1($t$+1) to Sk(t+1) of the respective members P1 to Pk from the current conversation amount Wij(t) and the stress state values S1($t$) to Sk(t) (step S18).

The group state prediction unit 22 derives the average value Sm of the future stress state values S1($t$+1) to Sk(t+1) of the respective members P1 to Pk (step S20), and when the average value Sm is equal to or lower than the threshold value Th (N in step S22), the process returns to step S12.

When the average value Sm is larger than the threshold value Th (Y in step S22), the derivation unit 24 specifies a pattern of the target conversation amount Wij_m(t) at which the average value Sm is minimized (step S24), and derives Wij_s(t)=Wij(t)−Wij_m(t) (step S26).

The proposal unit 26 urges the member Pi and the member Pj satisfying Wij_s(t)<0 to speak (step S28) and urges the member Pi and the member Pj satisfying Wij_s(t)>0 to be silent (step S30), and the process returns to step S12. When the instruction to end the process is input (Y in step S12), the process ends.

The method of determining a member to be proposed to change the conversation amount is not limited to the above example.

Figure 8:
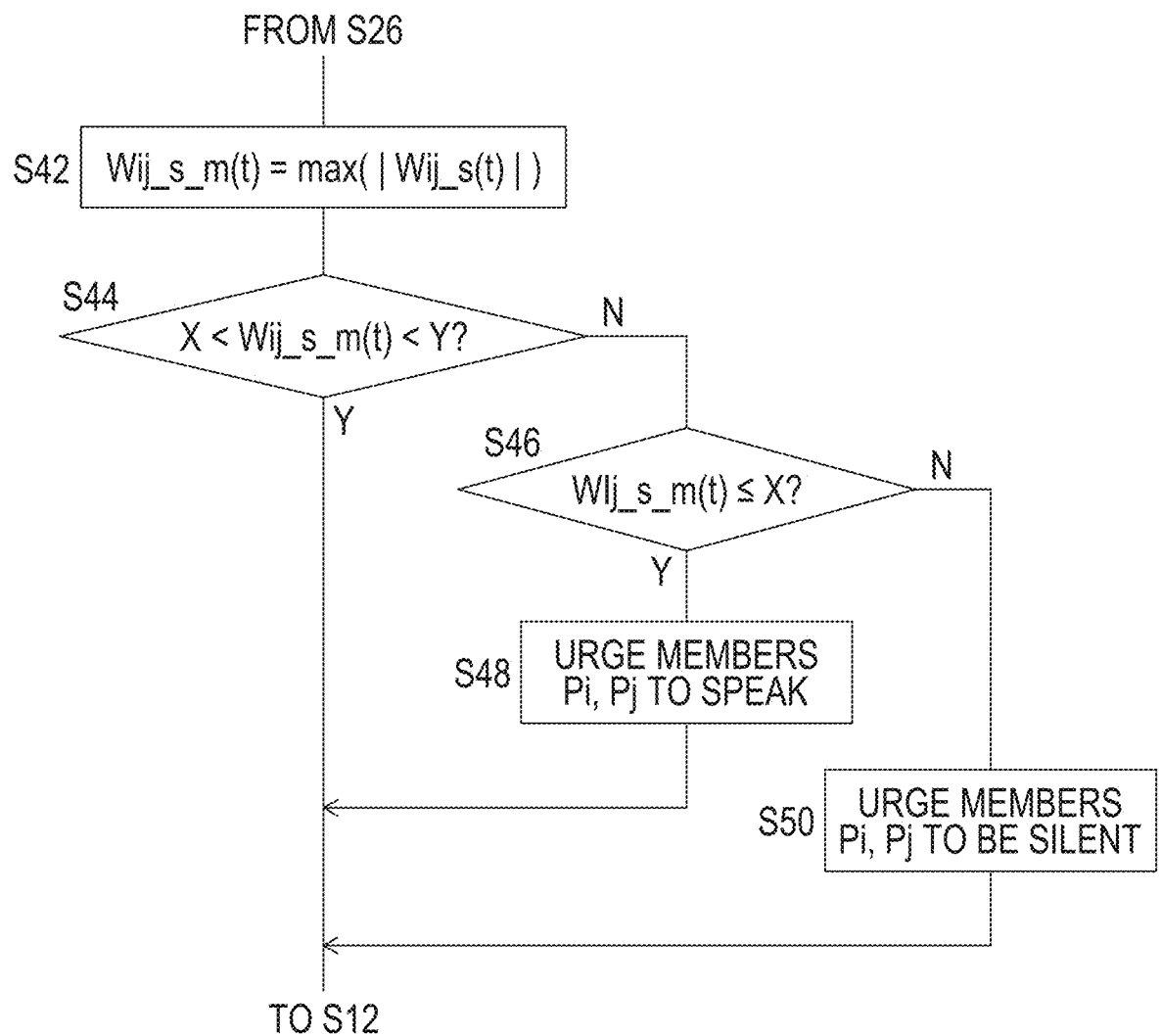
FIG. 8 is a flowchart showing another example of the communication support process.

FIG. 8 is a flowchart showing another example of the communication support process. Instead of steps S28 and S30 in FIG. 7, actions of steps S42 to S50 in FIG. 8 are executed.

Following step S26 in FIG. 7, the derivation unit 24 derives Wij_s_m(t)=max(|Wij_s(t)|) (step S42). max(|Wij_s(t)|) represents Wij_s(t) having the maximum absolute value. That is, the derivation unit 24 sets Wij_s(t) having the maximum absolute value as Wij_s_m(t).

When X<Wij_s_m(t)<Y (Y in step S44), the process returns to step S12. In this case, the proposal unit 26 does not propose a change in the conversation amount. X is a lower limit value and Y is an upper limit value, which can be appropriately determined by experiments or simulations. For example, X is a negative value and Y is a positive value. That is, when Wij_s_m(t) is close to zero, the proposal unit 26 does not propose the change in the conversation amount.

When X<Wij_s_m(t)<Y is not satisfied (N in step S44) and Wij_s_m(t)≤X is satisfied (Y in step S46), the proposal unit 26 urges the member Pi and the member Pj to speak (step S48), and the process return to step S12. When Wij_s_m(t)≤X is not satisfied (N in step S46), the proposal unit 26 urges the member Pi and the member Pj to be silent (step S50), and the process returns to step S12.

In the example, the change in the conversation amount is proposed for just two members who have the largest absolute values of the difference between the current conversation amount and the target conversation amount, and thus it is possible to make a proposal that can improve the future group state value Sm while the number of members to be proposed is minimized.

The action of step S44 may be omitted, and the decision of step S46 may be executed after step S42. In this case, the decision in step S46 is changed, and when Wij_s_m(t)<0 (step S46), the proposal unit 26 urges the member Pi and the member Pj to speak (step S48), and the process returns to step S12. When Wij_s_m(t)>0 (step S46), the proposal unit 26 urges the member Pi and the member Pj to be silent (step S50), and the process returns to step S12. When Wij_s_m(t)=0 (step S46), the process returns to step S12. Even in the modification example, it is possible to make a proposal that can improve the future group state value Sm while the number of members to be proposed is minimized.

Further, in the process of FIG. 7, in step S28, the proposal unit 26 may urge the member Pi and the member Pj satisfying Wij_s(t)<X to speak, and in step S30, the proposal unit 26 may urge the member Pi and the member Pj satisfying Wij_s(t)>Y to be silent. X and Y are the above-mentioned lower limit value and upper limit value. In the modification example, the members to be proposed can be limited to members who are predicted to contribute to the improvement of the future group state value Sm to a relatively large extent.

As described above, an example has been described in which, when the future stress state value Sm of the group G1 is larger than the threshold value Th, the pattern of the conversation amount that minimizes the stress state value Sm of the group G1 is set as the target conversation amount between the members P1 to Pk, however, the change in the conversation amount may be proposed without deriving the target conversation amount.

Specifically, the proposal unit 26 compares state propagation amounts from a plurality of others in the group G1 to the targeted member, and proposes a change in the communication amount between the targeted member and another person based on a comparison result such that the predicted future state value of the targeted member is improved. The proposal unit 26 specifies a positive and maximum state propagation amount from another person to the targeted member, and proposes a reduction in the communication amount between the member and the other person. By reducing the communication amount between the member and the other person, the state propagation amount from the other person to the member can be made smaller as compared with the communication amount before the reduction, and the future state value of the member can be made smaller.

The proposal unit 26 may specify a negative and minimum state propagation amount from another person to the targeted member, and propose an increase in the communication amount between the member and the other person. By increasing the communication amount between the member and the other person, the state propagation amount from the other person to the member can be made smaller as compared with the communication amount before the increase, and the future state value of the member can be made smaller.

In the modification example, the proposal unit 26 may decide whether or not there is a proposal for one or more members, and may not decide for all members. In this case, the member to be targeted for decision may be registered in the storage device 7 in advance by an administrator or the like, may be a member of which the influence degree λ of the other person on the state of the member is equal to or higher than a predetermined value, or may be a member having the maximum influence degree λ on the state of the member. The second acquisition unit 18 may acquire just the state propagation amount for the member to be targeted for decision, and the individual state prediction unit 20 may predict just the future stress state value of the member to be targeted for decision.

In the modification example, the change in the communication amount between the targeted member and another person is proposed, and thus it is possible to make the member find what measures should be taken to improve the future state of the member. In this way, it is possible to improve the future stress state value Sm of the group G1. Moreover, since the target conversation amount is not derived, it is possible to simplify the process.

Second Embodiment

In a second embodiment, a process of determining a member of the group G1 from among a plurality of persons such that a future group state value indicates a good state is added to the first embodiment. Hereinafter, the differences from the first embodiment will be mainly described.

Figure 9:
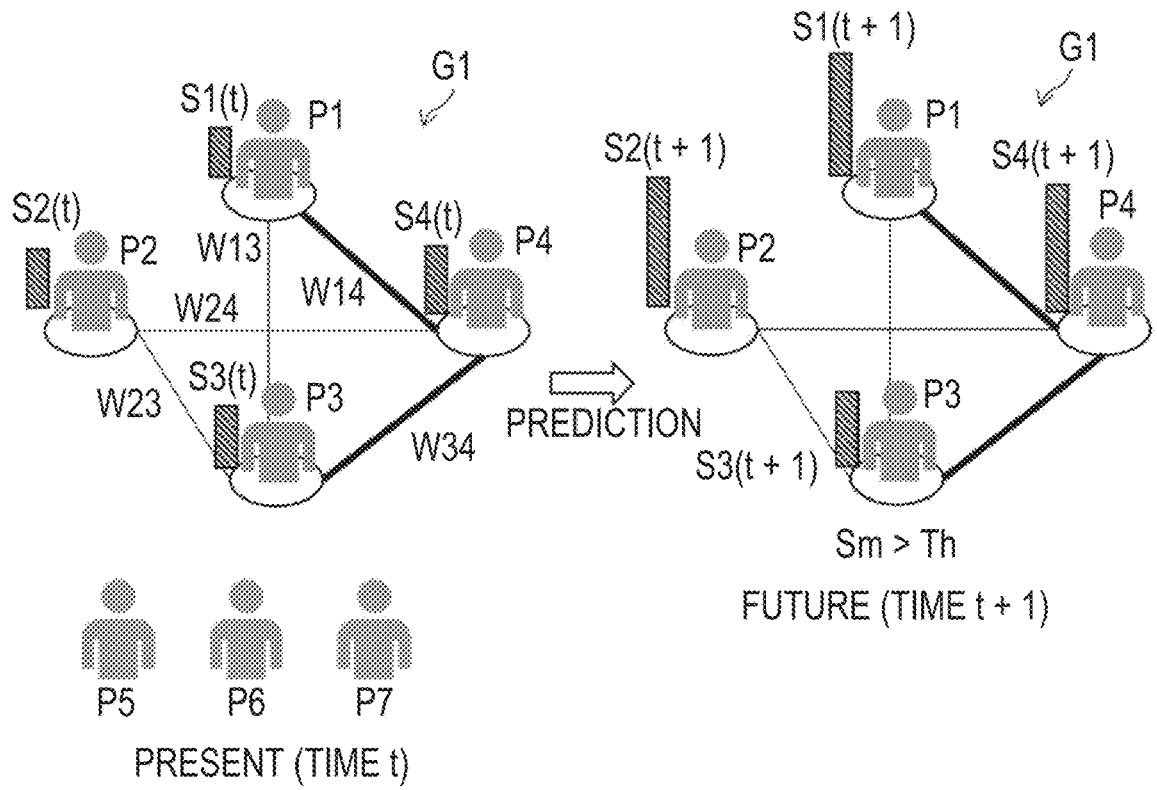
FIG. 9 is a diagram for describing a member determination function of a communication support system according to a second embodiment.

FIG. 9 is a diagram for describing a member determination function of the communication support system according to the second embodiment. Before the start of a meeting, the communication support system temporarily sets four members P1 to P4 who are candidates that constitute the group G1 from, for example, seven persons P1 to P7. At this point, the seven persons P1 to P7 do not have to be gathered at a communicable distance.

The communication support system acquires current state values $S1(t)$ to $S4(t)$ of the respective members P1 to P4, and state propagation amounts predicted based on past communication amounts W12, W13, W14, W23, W24, W34 between two members in each of a plurality of combinations for any two members drawn from the group G1. A method for deriving a state propagation amount is the same as that of the first embodiment, and the past communication amount may be used instead of the current communication amount.

For each of the members P1 to P4, the communication support system predicts a future state value indicating the future state of the member from the current state values $S1(t)$ to $S4(t)$ of the member and the state propagation amounts from a plurality of other members to the member. The communication support system predicts a future group state value Sm based on future state values $S1(t+1)$ to $S4(t+1)$. In the example of FIG. 9, it is assumed that the future group state value Sm is larger than a threshold value Th. In this case, the members P1 to P4 are not appropriate, and thus the communication support system temporarily sets another member. The communication support system repeats the temporary setting of a member until the future group state value Sm becomes equal to or lower than a threshold value Th.

Figure 10:
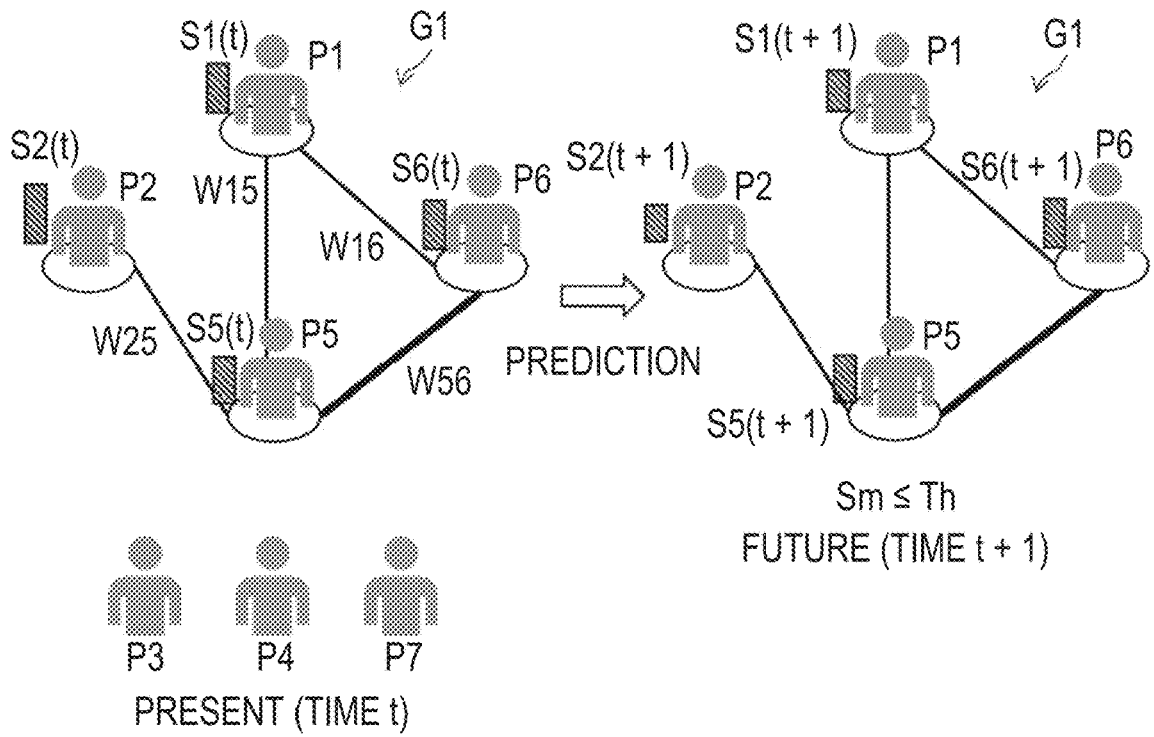
FIG. 10 is a diagram for describing the member determination function of the communication support system following FIG. 9.

FIG. 10 is a diagram for describing the member determination function of the communication support system following FIG. 9. The communication support system temporarily sets four members P1, P2, P5, P6 who are candidates that constitute the group G1 from the persons P1 to P7. Future state values $S1(t+1)$, $S2(t+1)$, $S5(t+1)$, $S6(t+1)$ of respective members newly predicted by the communication support system are different from the values in FIG. 9. It is assumed that the future group state value Sm is also smaller than the threshold value Th, unlike the value in FIG. 9. Therefore, the communication support system formally determines the members P1, P2, P5, P6 as members of the group G1 and notifies the determined members P1, P2, P5, P6. The members P1, P2, P5, P6 who have received the notification gather and start a meeting. Compared with the members P1 to P4 in FIG. 9, each of the members P1, P2, P5, P6 can easily maintain a good state during the meeting, and communication in the group G1 can be smoothly promoted. After the start of the meeting, the communication support system executes the process of the first embodiment.

Figure 11:
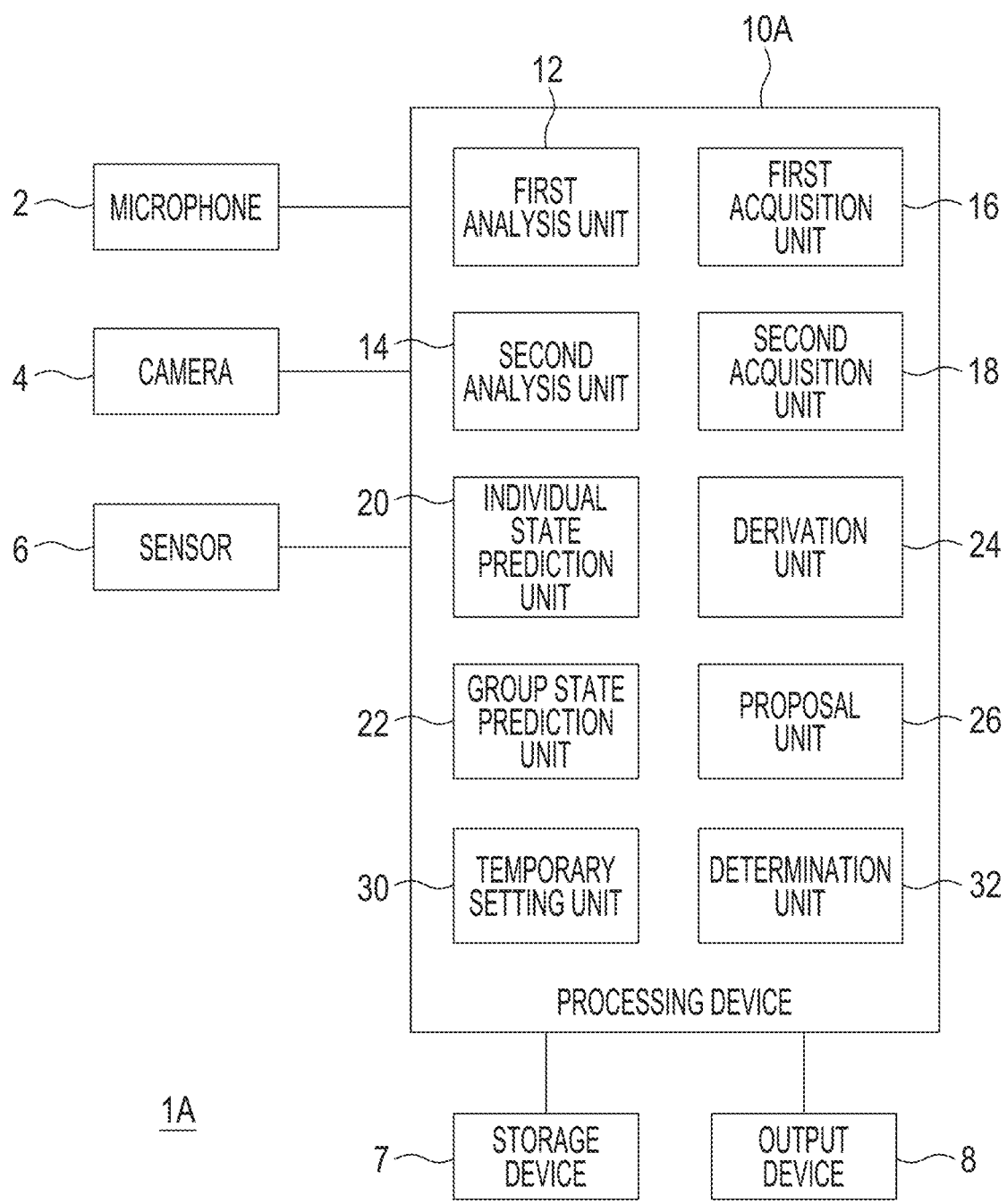
FIG. 11 is a diagram showing a configuration of the communication support system according to the second embodiment.

FIG. 11 is a diagram showing a configuration of a communication support system 1A according to the second embodiment. The communication support system 1A can also be called a "member determination system". In addition to the configuration shown in FIG. 3, the processing device 10A further includes a temporary setting unit 30 and a determination unit 32. An example in which the current state value and the future state value are stress state values and the communication amount is the conversation amount will be described. The processing device 10A is an example of the controller in the present disclosure.

The temporary setting unit 30 temporarily sets a plurality of persons who are candidates that constitute the group G1. The first acquisition unit 16 acquires a current stress state value of each of the temporarily set persons.

The second acquisition unit 18 acquires a past conversation amount between the person and another person in the group G1 for each of the temporarily set persons, and acquires a state propagation amount indicating a state amount propagated from the other person to the person, which is predicted based on the acquired past conversation amount. The storage device 7 stores the past conversation amount between two registered users for each of a plurality of combinations for any two registered users. The second acquisition unit 18 acquires the past conversation amount from the storage device 7.

For each of the temporarily set persons, the individual state prediction unit 20 predicts a future stress state value of the person from the acquired current stress state value of the person and the acquired state propagation amount for the person.

The group state prediction unit 22 predicts the future stress state value Sm of the group G1 based on the predicted future stress state value of each of the persons.

When the predicted future stress state value Sm of the group G1 satisfies a predetermined condition regarding a good state, the determination unit 32 determines the temporarily set persons as members of the group G1, and causes the output device 8 to output information for specifying the determined members.

When the future stress state value Sm of the group G1 does not satisfy a predetermined condition regarding the good state, the temporary setting unit 30 newly temporarily sets a plurality of persons who are candidates that constitute the group G1, and the first acquisition unit 16, the second acquisition unit 18, the individual state prediction unit 20, the group state prediction unit 22, and the determination unit 32 perform the above process again.

Figure 12:
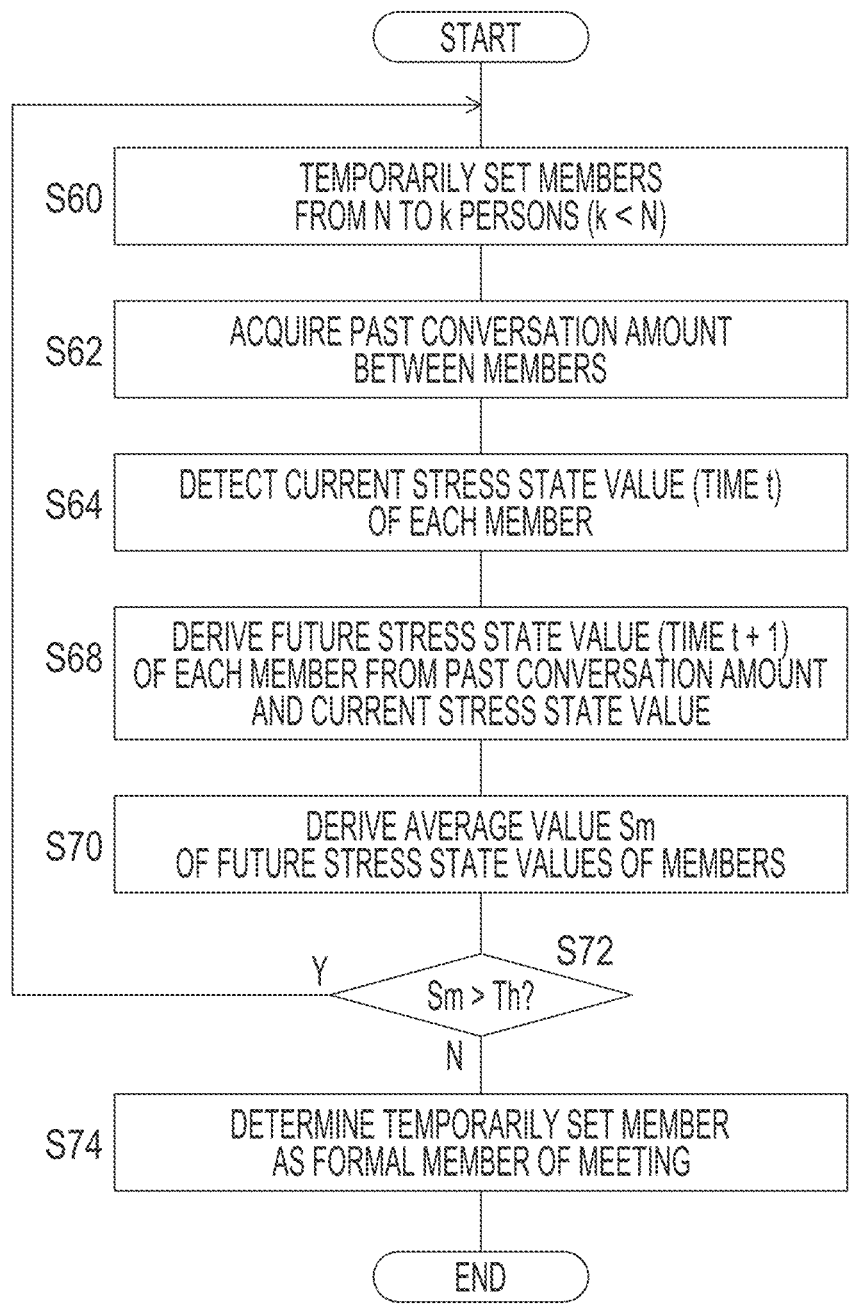
FIG. 12 is a flowchart showing a member determination process of the communication support system of FIG. 11.

FIG. 12 is a flowchart showing a member determination process of the communication support system 1A of FIG. 11. The temporary setting unit 30 temporarily sets members from N to k persons (k<N) (step S60). The second acquisition unit 18 acquires the past conversation amount between the members (step S62), and the first analysis unit 12 detects the current stress state value of each member (step S64). The individual state prediction unit 20 derives the future stress state value of each member from the past conversation amount and the current stress state value (step S68).

The group state prediction unit 22 derives the average value Sm of the future stress state values of k members (step S70), and when the average value Sm is larger than the threshold value Th (Y in step S72), the process returns to step S60. When the average value Sm is equal to or lower than the threshold value Th (N in step S72), the determination unit 32 determines the temporarily set member as a formal member of the meeting (step S74), and the process is ended.

During the member determination process, k may be a predetermined constant value, or k may be changed when the average value Sm is larger than the threshold value Th (Y in step S72). When k is changed when the average value Sm is larger than the threshold value Th (Y in step S72), the temporary setting unit 30 may increase k by a predetermined number or decrease k by a predetermined number, and then execute the action of step S10.

According to the embodiment, it is possible to determine a plurality of members who are expected to have a relatively improved future state of the group G1 by communication, from among a plurality of persons.

The present disclosure has been described above based on the embodiments. It should be noted that the embodiments are merely an example, and it is understood by those skilled in the art that various modification examples can be made to the combination of the components and processes thereof, and that such modification examples are also within the scope of the present disclosure.

For example, the derivation unit 24 and the proposal unit 26 don't have to be provided and the change in the communication amount does not have to be proposed. In this case, the first acquisition unit 16 causes the output device 8 to output the current state value of the individual such that the individual can specify the current state value, and the individual state prediction unit 20 causes the output device 8 to output the future state value of the individual. The output device 8 may display, for example, FIG. 1 as an image. Since prediction as to whether the state of the individual in the future will deteriorate can be made based on the output current state value and future state value, it is possible to specify whether some measures regarding communication are needed to be taken for the individual. Therefore, keeping the future state of the individual in a good state is made easy. Alternatively, the individual state prediction unit 20 may cause the output device 8 to output the future state value of the individual such that the individual can specify the future state value, just when the future state value of the individual is larger than the threshold value. Further, the group state prediction unit 22 may cause the output device 8 to output the future group state value, and may cause the output device 8 to output the future group state value just when the future group state value is larger than the threshold value. Since prediction as to whether the state of the group G1 in the future will deteriorate can be made based on the future group state value, it is possible to specify whether some measures regarding communication are needed to be taken for the group G1.

What is claimed is:

1. A state prediction system comprising a controller configured to acquire a current state value indicating a current state of a targeted individual in a group, acquire a state propagation amount indicating a state amount propagated from another person in the group to the targeted individual by communication between the targeted individual and the another person, predict a future state value indicating a future state of the targeted individual from the acquired current state value of the targeted individual and the acquired state propagation amount, acquire, as information, a current state value indicating a current state of the another person, a current communication amount between the targeted individual and the another person, and a degree of influence of the another person on a state of the targeted individual, and derive the state propagation amount from the another person to the targeted individual based on the acquired information.

2. The state prediction system according to claim 1, wherein the controller is configured to derive, as the state propagation amount from the another person to the targeted individual, a product of the current state value of the another person, the current communication amount between the targeted individual and the another person, and the degree of the influence of the another person on the state of the targeted individual, and derive, as the future state value of the targeted individual, a sum of the current state value of the targeted individual and the state propagation amount from the another person to the targeted individual.

3. The state prediction system according to claim 1, wherein the controller is configured to for each of a plurality of another persons in the group, derive, as the state propagation amount from the another person to the targeted individual, a product of the current state value of the another person, the current communication amount between the targeted individual and the another person, and the degree of the influence of the another person on the state of the targeted individual, and derive, as the future state value of the targeted individual, a total sum of the current state value of the targeted individual and state propagation amounts from the another persons to the targeted individual.

4. The state prediction system according to claim 1, wherein the controller is configured to for each of a plurality of another persons in the group, acquire the state propagation amount from the another person to the targeted individual, and compare the acquired state propagation amounts from the another persons to the targeted individual and, based on a comparison result, propose a change in a communication amount between the targeted individual and the another person such that the future state value of the targeted individual is improved.

5. The state prediction system according to claim 1, wherein the controller is configured to predict a future state value of each of a plurality of persons in the group, and predict a future group state value indicating a future state of the group based on the predicted future state value of each of the persons.

6. The state prediction system according to claim 5, wherein the controller is configured to derive a target communication amount between the persons such that the predicted future group state value is improved, and compare a current communication amount between two targeted persons in the group with the target communication amount and propose a change in a communication amount based on a comparison result.

7. A member determination system comprising a controller configured to temporarily set a plurality of persons who are candidates that constitute a group, for each of the temporarily set persons, acquire a current state value indicating a current state of the person, for each of the temporarily set persons, acquire a state propagation amount indicating a state amount propagated from another person in the group to the person, the state amount being predicted based on a past communication amount between the person and the another person, for each of the temporarily set persons, predict a future state value indicating a future state of the person from the acquired current state value of the person and the acquired state propagation amount to the person, predict a future group state value indicating a future state of the group based on the predicted future state value of each of the persons, and when the predicted future group state value satisfies a predetermined condition for a good state, determine the temporarily set persons as members of the group.

8. A state prediction method that is executed by a computer, the state prediction method comprising:

acquiring a current state value indicating a current state of a targeted individual in a group;

acquiring a state propagation amount indicating a state amount propagated from another person in the group to the targeted individual by communication between the targeted individual and the another person;

predicting a future state value indicating a future state of the targeted individual from the acquired current state value of the targeted individual and the acquired state propagation amount;

acquiring, as information, a current state value indicating a current state of the another person, a current communication amount between the targeted individual and the another person, and a degree of influence of the another person on a state of the targeted individual, and deriving the state propagation amount from the another person to the targeted individual based on the acquired information.

* * * * *